(12) United States Patent
Voelker

(10) Patent No.: US 6,248,091 B1
(45) Date of Patent: Jun. 19, 2001

(54) BALLOON CATHETER

(76) Inventor: Wolfram Voelker, Leberstrasse 81, 69469 Weinheim (DE)

( * ) Notice: Subject to any disclaimer, the term of this patent is extended or adjusted under 35 U.S.C. 154(b) by 0 days.

(21) Appl. No.: 09/194,853

(22) PCT Filed: Jun. 3, 1997

(86) PCT No.: PCT/EP97/02864

§ 371 Date: Dec. 2, 1998

§ 102(e) Date: Dec. 2, 1998

(87) PCT Pub. No.: WO97/46270

PCT Pub. Date: Dec. 11, 1997

(30) Foreign Application Priority Data

Jun. 4, 1996 (DE) .............................................. 196 22 335

(51) Int. Cl.[7] .................................................. A61M 29/00
(52) U.S. Cl. ............................................. 604/96; 604/151
(58) Field of Search ................................ 604/96, 151, 22, 604/523, 4, 8, 101.01, 101.02, 123; 600/16

(56) References Cited

U.S. PATENT DOCUMENTS

| | | | |
|---|---|---|---|
| 4,631,052 | * 12/1986 | Kensey | 604/22 |
| 4,729,763 | * 3/1988 | Henrie | 604/22 |
| 4,753,221 | 6/1988 | Kensey et al. . | |
| 4,857,046 | * 8/1989 | Stevens et al. | 604/22 |
| 5,137,513 | * 8/1992 | McInnes et al. | 604/96 |
| 5,163,910 | 11/1992 | Schwartz et al. . | |
| 5,628,719 | 5/1997 | Hastings et al. . | |

FOREIGN PATENT DOCUMENTS

PCT/NL92/00159   9/1992 (WO) .

* cited by examiner

*Primary Examiner*—Richard K. Seidel
*Assistant Examiner*—Kevin C. Sirmons
(74) *Attorney, Agent, or Firm*—Fulwider Patton Lee & Utecht, LLP

(57) ABSTRACT

The balloon catheter has a catheter hose (10) and a hydraulically expandable balloon (14) on a balloon support (13). Between the catheter hose (10) and the catheter support (13), there is a small-diameter pump (16) which takes blood in through lateral inlets (21) and pumps it through the tubular balloon support (13). The pump (16) is driven by a flexible shaft (23) running through the catheter hose (10) or by a directly integrated micromotor.

10 Claims, 2 Drawing Sheets

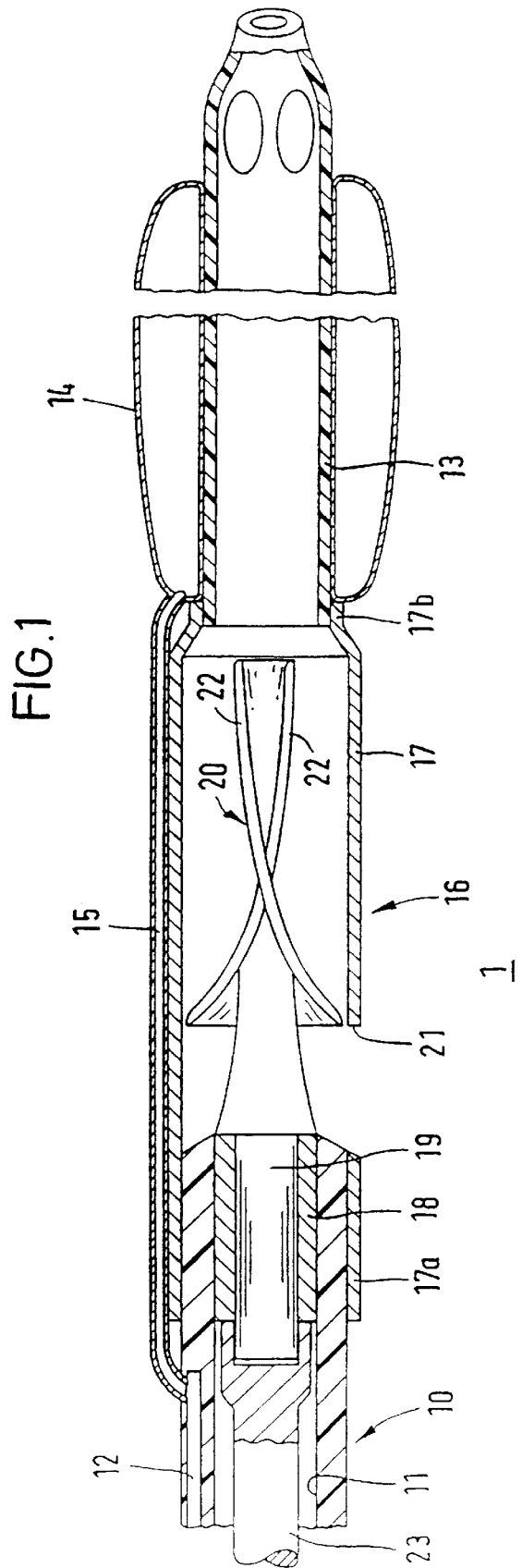

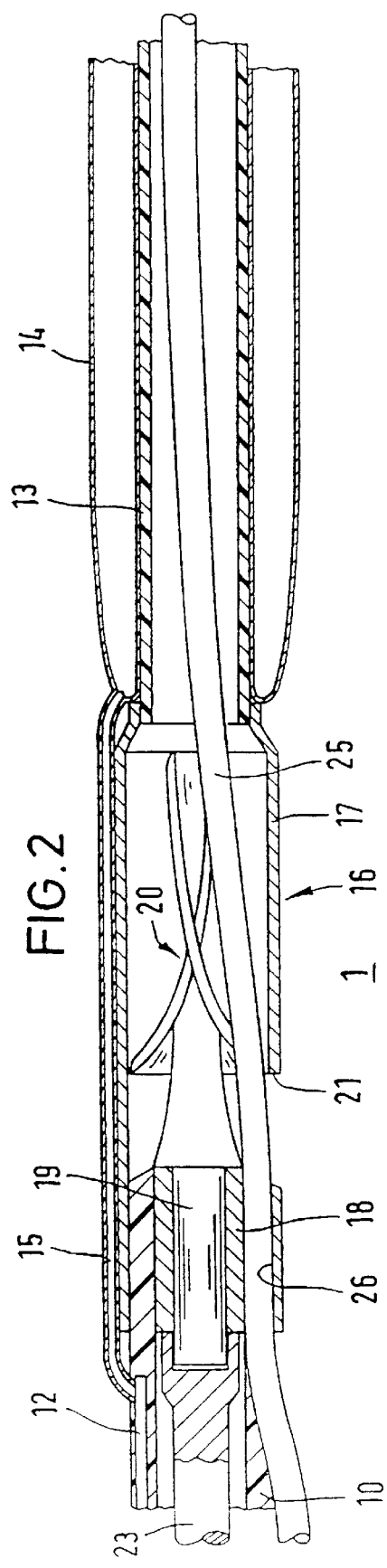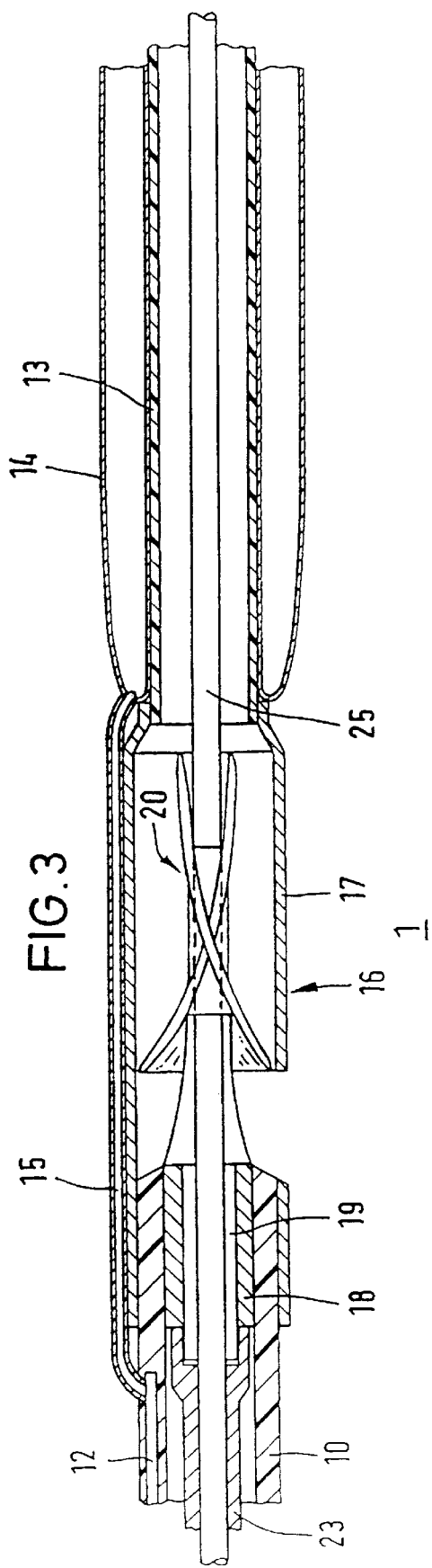

BALLOON CATHETER

The present invention refers to a balloon catheter adapted for insertion into a blood vessel to, for example, expand obstructions in vessels or to temporarily isolate a portion of the blood vessel wall from contact with the blood flow.

Balloon catheters are known comprising a catheter hose having its distal end provided with a tubular balloon support with an angular balloon fitted thereon. A lumen extending through the catheter hose communicate the balloon with an extracorporeal pressure source. The balloon is expanded by feeding a pressurized liquid thereinto. A complete obstruction of the blood vessel usualy occurs in doing so, resulting in an inadequate supply (ischemia) to the downstream organ regions. To avoid this, perfusion catheters (circulation catheters) are used. Among these are auto-perfusion cathaters (DE 92 07 395 U1) with a passage through the balloon support so that blood can circulate through the interior of the angular balloon, as well as active perfusion systems, wherein an external high-pressure pump connected to the distal catheter end provides for a continuous perfusion through the interior of the cathater. In contrast to auto-perfusion cathaters, active perfusion systems actively develop a particular pressure that is independent from the momentary blood pressure of a patient. To do so, however, arterialized blood has to be drawn from the patient that is pumped outside the body into the lumen of the cathater hose. Moreover, due to the high pressure losses within the small-lumen cathater hose, very high pump pressures (up to about 12 bar) are necessary to convey about 40 to 60 ml/min.

From U.S. Pat. No. 4 969 865, an intravascular blood pump for cardiac support is known. This blood pump may be introduced into the heart through a blood vessel. It comprises an elongate tube accommodating a screw-type impeller driven by a flexible shaft. This pump has an axial intake and has its opposite outlet end provided with holes for the radial outflow. In operation, the blood pump is positioned in the opening of the cardiac valve, with the intake end being located in one of the cardiac ventricles, while the delivery end is disposed in the aorta.

It is an object of the present invention to provide a balloon cathater that forms a simplified active perfusion system.

According to the invention, the object is solved with the features of claim 1.

In the present balloon cathater, a pump is disposed in the course of the cathater, in particular at a position proximal of the balloon support. Through appropriate openings, the pump draws blood laterally from the blood vessel and pumps is axially through the balloon support. Since the pump is disposed just in front of the balloon support, only a relatively low pump pressure is required. The pump is small enough to be located in the cathater immediately in the area of the surgical operation, i.e. close to the balloon, so that the length of the lumen to be flushed is short, thereby maintaining the pressure losses on a relatively low level. The diameter of the pump is so small that it can be inserted into the blood vessel together with the cathater, without injuring the blood vessel. Generally, smaller blood vessels are treated with balloon cathaters. The maximum diameter of the pump should not exceed about 1.4 mm. Such a small pump can be integrated into the cathater so that it is situated just in front of the balloon support extending through the site of the treatment of the blood vessel. Here, the pump draws blood in the flow direction of the vessel from the high pressure region via at least one lateral inlet and conveys the same into the low pressure region beyond the expanded balloon.

Due to the required compact size of the pump, it has to be driven at relatively high rotational speeds, so as to achieve the necessary delivery rate of, for example, 60 $cm^3$/min. Preferably, the rotary speed of the pump is within the range from 80,000 to 150,000 rpm.

Preferably, the balloon cathater is used for expanding obstructions in vessels, in particular in the coronary vessel area, in the carotid artery, and the like. Yet, it is also possible to position a wire basket (stent) to distend obstructions in vessels.

Another aspect of the invention refers to a perfusion cathater comprising a plurality of serially arranged balloons. The balloons temporarily seal a length of the vessel to allow for a bypass to be sutured to this area. Blood keeps flowing through the tubular balloon support, while the sealed vessel section is available for surgery.

The invention provides an active perfusion cathater with an integrated pump. The handling of the same largely corresponds to that of passive auto-perfusion cathaters, yet its performance is similar to that of active perfusion systems. It is another advantage that the balloon support can be formed with a very small outer diameter of about 1 mm. Thus, it is guaranteed in almost any case, even with severe stenoses that the balloon portion can be placed in the stenosis.

Preferably , the pump is driven by a flexible shaft connected to a motor provided at the proximal end of the cathater hose. Such pumps comprising only a pump housing and an impeller rotatingly housed therein, can be manufactured with a very small outer diameter of about 1.5 min. In general, the invention also provides for integrating a pump motor in the cathater in the immediate vicinity of the pump, the motor directly driving the impeller wheel, in this case.

In order to place a balloon cathater in a blood vessel, a guide wire is usualy inserted over which the cathater is then pushed. Such placement using a guide wire is also possible with the present balloon cathater. Here, however, the guide wire has to be passed through the pump. The impeller of the pump or the pump itself is accordingly designed such that it allows for the passage of a guide wire having a diameter of about 0.3 mm. It should be taken into consideration that the pump is started up only after the guide wire has b e en withdrawn far enough from the immediate pump area. While placing the catheter, it is acceptable that the guide wire blocks the impeller wheel.

The following is a detailed description of embodiments of the present invention taken in conjunction with the accompanying drawings.

In the Figures:

FIG. 1 illustrates a longitudinal section through the distal end portion of the balloon cathater of a first embodiment, FIG. 2 shows the balloon cathater of FIG. 1 with a guide wire inserted, the pump forming a mono-rail guide, and FIG. 3 illustrates an embodiment wherein the guide wire passes coaxially through the pump.

The balloon cathater 1 of FIG. 1 comprises an elongate cathater hose 10 of about 1 m in length and about 1.3 mm in diameter. The flexible cathater hose 10 has a central hose lumen 11 of about 0.8 mm in diameter. Further, another lumen 12 extends through the wall of the cathater hose 10 for supplying pressure fluid to the balloon 14.

Situated at the cathater tip is the tubular balloon support 13 having an inner diameter of about 0.8 mm and an outer diameter of about 1.0 mm. This balloon support 13 is enclosed by at least one balloon 14. The balloon 14 is communicated with the lumen 12 of the cathater hose 10 through a conduit 15. The front end of the balloon support 13 is tapered and has one axial and a plurality of lateral blood outlet openings.

The pump 16 is located between the cathater hose 10 and the balloon support 13. The pump has a tubular pump housing 17 with an outer diameter of about 1.5 mm. the proximal end 17a of the pump housing is fastened to the end of the cathater hose 10 and the distal end 17b is connected to the balloon support 13. The pump housing 17 is made of metal and holds a bearing 18 in which the shaft 19 of the impeller wheel 20 is supported. The end of the cathater hose 10 is fitted between the bearing 18 and the pump housing 17. Immediately next to the end of the cathater hose 10, lateral inlets 21 are provided in the housing 17, through which blood may enter the pump housing 17 radially. In the area of the impeller wheel 20, circumference of the housing 17 is closed. The impeller wheel 20 has a plurality of blades 22 helically arranged about the axis and extending over an angular range of at least 150°. The length of the impeller wheel 20 is about twice the maximum diameter of the impeller wheel. The impeller wheel 20 ends just in front of the balloon support 13.

The shaft 19 of the impeller wheel 20 is connected to a flexible shaft 23 extending within the lumen 11 of the cathater hose 10 and having its proximal end connected with an external electric motor driving the shaft at a rotational speed in the order of 100,000 rpm.

While the balloon portion of the cathater has been inserted, for example, into the area of a stenosis, the balloon 14 has been pressurized and thereby inflated, the pump 16 conveys blood from the inlets 21 through the balloon support 13. The distal end of the balloon support 13 is open or provided with openings so that, at this location, the blood can flow from the balloon support 13 into the blood vessel.

The embodiment of FIG. 2 differs from that of FIG. 1 only in that a guide wire 25 is added that is placed first in the blood vessel and over which the cathater is then slipped. This flexible guide wire 25 extends generally outside the cathater hose 10. At the distal end of the cathater hose, preferably on the last 10 cm of the cathater hose 10 and in a part of the pump housing 17, a longitudinally extending channel 26 is provided that forms a guide portion (monorail) through which the guide wire 25 is guided into the pump housing 17. The diameter of the guide wire is about 0.3 mm so that the guide wire can extend through the impeller wheel 20 passing between its blades. While the guide wire 25 is in the pump housing, the impeller wheel is not rotated. After having placed the cathater, the guide wire is withdrawn from at least the pump housing to allow for treatment. Here, the position of the channel 26 and the design of the impeller wheel 20 are such that the guide wire 25 can always be pushed again through the balloon support 13 towards the balloon via the standing impeller wheel 20 so as to replace the system at another position using the guide wire 25, without having to entirely withdraw the balloon for this purpose.

In the embodiment of FIG. 3, the guide wire 25 extends coaxially through the flexible shaft 23, the shaft 19 and the impeller wheel 20. These parts have corresponding axial channels to be slipped over the guide wire (over-the-wire technique). When the pump is operated, the guide wire may be withdrawn to improve the throughflow through the balloon support 13. After the guide wire has been withdrawn, it may be advanced again, if the position of the cathater is to be changed. However, this is not essential for the operation of the pump.

If a plurality of balloons are provided on the balloon support, a hydraulic supply line 15 passing beyond the pump 16 may be arranged for each balloon. Nevertheless, the thickest part of the cathater, i.e. the portion of the pump 16, should not substantially exceed a diameter of 1.5 mm, in particular for use in the coronary area (carotids), since otherwise the cathater can not be placed using a standard introduction cathater having a 2 mm diameter. Moreover, it is necessary that the length of the pump housing 17 does not exceed about 6 mm.

The embodiments described above refer to a balloon cathater comprising a pump 16 operating according to the low-pressure principle, which is arranged close to the balloon cathater, i.e. at the end of the cathater hose. In this case, the pump needs to generate but a comparatively low pressure. It is also contemplated within the scope of the present invention to provide an intravascular pump in the course of the cathater hose, having a greater distance from the balloon support. Such a pump has to deliver a higher pump pressure because of the pressure drop developing across the cathater hose.

What is claimed is:

1. A balloon cathater, comprising:
   a cathater hose (10);
   a tubular balloon support (13) connected to the cathater hose and calTying at least one expandable balloon (14);
   a pump (16) having an impeller wheel, integrated within said cathater and disposed in the area between the cathater hose (10) and the balloon support (13), the pump drawing blood through at least one lateral inlet (21) and delivering it axially into the balloon support (13); and
   a longitudinal guide channel (26) for a guide wire (25) having means for positioning a guide wire to be extendible through said impeller wheel.

2. The balloon cathater of claim 1, further comprising a guide wire (25) and characterized in that the guide wire (25) extends substantially outside the cathater hose (10) and that the guide channel (26) leads into the pump (16).

3. The balloon cathater of claim 1, wherein said pump includes an impeller wheel having blades, characterized in that the guide channel (26) extends from the proximal end of the cathater hose to the proximal end of the blades of the impeller wheel (20).

4. The balloon cathater of claim 1, further comprising a guidewire (25) that extends within the cathater hose (10) and coaxially through the pump.

5. The balloon cathater of one of claims 1–4, characterized in that the pump (16) is driven by a flexible shaft (23) connected with a motor arranged at the proximal end of the cathater hose (10).

6. The balloon cathater of one of claims 1–4, characterized in that the pump (16) is driven by a motor arranged along the length of the cathater hose.

7. The balloon cathater of one of claims 1, characterized in that the pump (16) comprises an impeller wheel (20) with at least one blade (22), the length of which is at least equal to the maximum diameter of the impeller wheel (20).

8. The balloon cathater of one of claims 1, characterized in that the lateral inlets (21) are at least partly spaced from the vessel wall when the balloon (14) is inflated.

9. The balloon cathater of claim 8, characterized in that the lateral inlets (21) and the balloon (14) are separated by a distance of at most equal to the length of the blades of the impeller wheel (20).

10. The balloon of cathater of claim 1, characterized in that at least two mutually spaced balloons are arranged on the balloon support.

* * * * *

UNITED STATES PATENT AND TRADEMARK OFFICE
CERTIFICATE OF CORRECTION

PATENT NO. : 6,248,091 B1
DATED : June 19, 2001
INVENTOR(S) : Wolfram Voelker

It is certified that error appears in the above-identified patent and that said Letters Patent is hereby corrected as shown below:

Column 1,
Lines 16, and 60 replace "cathaters" with -- catheters --.
Lines 21-23, 27, 29, 42, 46-47, 53, 58, and 62, replace "cathater" with -- catheter --.

Column 2,
Lines 6, 12, 17, 28, 32, 34-35, 37, 51-52, 56-58, 60, 62, and 66, replace "cathater" with catheter --.
Line 19, replace "cathaters" with -- catheters --.

Column 3,
Lines 7, 10, 12, 24, 27, 36, 38-39, 47, and 63, replace "cathater" with -- catheter --.

Column 4,
Lines 3, 5-6, 10, 12, (both occurrences), 16-17, 20-22, 25-26, 33, 35, 37, 40, 42-45, 48-49, 51, 52, 56, 59, and 63, replace "cathater" with catheter --.

Signed and Sealed this

Twelfth Day of March, 2002

Attest:

Attesting Officer

JAMES E. ROGAN
Director of the United States Patent and Trademark Office